(12) United States Patent
Maa et al.

(10) Patent No.: US 10,881,752 B2
(45) Date of Patent: Jan. 5, 2021

(54) ANTI-BACTERIAL PHOTOCATALYTIC COATING APPARATUS AND PROCESS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 249 days.

(21) Appl. No.: 16/222,860

(22) Filed: Dec. 17, 2018

(65) Prior Publication Data

US 2019/0336631 A1 Nov. 7, 2019

Related U.S. Application Data

(63) Continuation-in-part of application No. 15/969,987, filed on May 3, 2018, now abandoned.

(51) Int. Cl.
| | |
|---|---|
| *A61L 2/18* | (2006.01) |
| *B05D 3/06* | (2006.01) |
| *B05D 1/12* | (2006.01) |
| *C09D 5/16* | (2006.01) |
| *A61L 2/14* | (2006.01) |
| *A61L 2/10* | (2006.01) |

(52) U.S. Cl.
CPC ............... *A61L 2/18* (2013.01); *A61L 2/10* (2013.01); *A61L 2/14* (2013.01); *B05D 1/12* (2013.01); *B05D 3/067* (2013.01); *C09D 5/1618* (2013.01); *A61L 2202/11* (2013.01); *A61L 2202/13* (2013.01); *B05D 2301/00* (2013.01); *B05D 2601/28* (2013.01)

(58) Field of Classification Search
None
See application file for complete search history.

(56) References Cited

U.S. PATENT DOCUMENTS 9,522,384 B2   12/2016   Lu et al.
2015/0194237 A1*  7/2015  Ranganathan ......... H01B 5/002
                                                    174/40 R

* cited by examiner

*Primary Examiner* — Kishor Mayekar
(74) *Attorney, Agent, or Firm* — Han IP PLLC; Andy M. Han

(57) ABSTRACT

An anti-bacterial photocatalytic coating apparatus includes a chassis and a container containing an anti-bacterial photocatalytic coating liquid. There is a means mounted on the chassis for applying plasma-based surface activation unto a stationary surface underneath the chassis. There is also a means mounted on the chassis for spraying the anti-bacterial photocatalytic coating liquid on the surface underneath the chassis. A third means mounted on the chassis for shining UV light onto the surface sprayed with the anti-bacterial photocatalytic coating liquid. Optionally, there is a means mounted on the chassis for baking the surface sprayed with the anti-bacterial photocatalytic coating liquid. The plasma-based surface activation may be replaced with the spraying of a non-photocatalytic prime coating. The equivalent anti-bacterial photocatalytic coating processes for coating stationary surface are also introduced.

14 Claims, 4 Drawing Sheets

ANTI-BACTERIAL PHOTOCATALYTIC COATING APPARATUS AND PROCESS

CROSS REFERENCE TO RELATED PATENT APPLICATION

The present disclosure is a Continuation-in-Part (CIP) of U.S. patent application Ser. No. 15/969,987, filed on May 3, 2018, the content of which is herein incorporated by reference in its entirety.

BACKGROUND

Technical Field

The present disclosure pertains to the field of anti-bacterial photocatalytic coating devices and process.

Description of Related Art

Photocatalysts are known to become active under ultraviolet light and kill bacteria by breaking down the cell wall of the bacteria. Recently technology advancement on photocatalysts has discovered means to activate the anti-bacterial photocatalytic effect with visible light. In U.S. patent application Ser. No. 15/969,987, the inventors applied photocatalytic coating to attachable devices. The attachable photocatalytic device can be attached over the surface of a carrier, thus providing anti-bacterial protection to the carrier. Such attachable anti-bacterial photocatalytic device are suitable for flat surface such as table and computer screen, but with limited size. For large stationary surface areas such as floor or tabletop or countertop, however, it is not practicable to use attachable anti-bacterial photocatalytic device over them. It may be possible to use new floor tiles with coated anti-bacterial photocatalytic film for new construction or renovation work. For floor area that is currently in use, it may be cost-prohibited for installing new floor tile with anti-bacterial photocatalytic film. Putting in new floor tile would also disrupt the use of the floor area affected by the installation. Moreover, the anti-bacterial photocatalytic coating film on a floor tile may be worn off through normal use, e.g., due to foot traffic. So using floor tile coated with anti-bacterial photocatalytic film can't provide a permanent anti-bacterial protection of the floor. There is a need for a better solution that could not only enhance the floor tiles in use with anti-bacterial functionality, but also enable the re-application of the anti-bacterial photocatalytic coating as needed for maintaining a sufficient level of anti-bacterial photocatalytic protection at all time.

SUMMARY

The present disclosure introduces an anti-bacterial photocatalytic coating apparatus that applies anti-bacterial photocatalytic coating over large stationary surface areas. Also introduced in the present disclosure is an anti-bacterial photocatalytic coating process over large stationary surface areas.

In one aspect, the anti-bacterial photocatalytic coating apparatus comprises a chassis and a container containing an anti-bacterial photocatalytic liquid. There is a means mounted on the chassis for applying plasma-based surface activation unto a stationary surface underneath the chassis. There is second means mounted on the chassis for spraying the anti-bacterial photocatalytic coating liquid on the surface underneath the chassis. There is a third means mounted on the chassis for shining an ultraviolet (UV) light onto the surface sprayed with the anti-bacterial photocatalytic coating liquid. Optionally, there is fourth means mounted on the chassis for baking the surface sprayed with the anti-bacterial photocatalytic coating liquid. Moreover, the chassis is movable. Some of the surface area is protected by polishing coating, which makes it hard for an anti-bacterial photocatalytic coating material to form a strong binding or adherence with the surface. Plasma surface activation is used to break loose the polishing coating on the stationary surface through plasma, thus preparing the surface for anti-bacterial photocatalytic coating. UV light is used after spraying of the anti-bacterial photocatalytic coating liquid for two reasons. Firstly, UV light activates the anti-bacterial photocatalytic activities of the photocatalytic particle. Secondly, the UV light helps the photocatalytic particle forming a finer and better binding at the chemical level with the surface material. Baking process may be used for two benefits. Firstly, it may shorten the time for the anti-bacterial photocatalytic coating liquid to dry up, as compared to natural curing. Secondly, the baking can enhance the binding between the photocatalytic particles with the surface material. However, baking is not required for surface material with plenty of spores, such as some wooden floor. The temperature and the duration of baking varies from one surface material to another.

The plasma-based surface activation is effective in activating plastic and rubber surface. It is ineffective against ceramic, terra cotta, granite, or other concrete tiles. With this surface materials, it is necessary to apply a prime coating film on the surface first before the spraying of the anti-bacterial photocatalytic coating liquid such that the prime coating film adheres better with the underlying surface material and at the same time forms a strong binding with the photocatalytic material. Therefore, in another aspect of the present disclosure, the anti-bacterial photocatalytic coating apparatus comprises a chassis, a container containing an anti-bacterial photocatalytic liquid, and another container containing a non-photocatalytic prime coating liquid. There is a means mounted on the chassis for spraying the non-photocatalytic prime coating liquid on a stationary surface underneath the chassis. There is second means mounted on the chassis for spraying the anti-bacterial photocatalytic coating liquid on the surface underneath the chassis. There is a third means mounted on the chassis for shining UV light onto the surface sprayed with the anti-bacterial photocatalytic coating liquid. Optionally, there is fourth means mounted on the chassis for baking the surface sprayed with the anti-bacterial photocatalytic coating liquid.

In some embodiments, there is a means mounted to the chassis for moving the chassis on the stationary surface. One example of such a means is wheels. It enables the anti-bacterial photocatalytic coating apparatus to be movable. In some other embodiments, the chassis is portable by hand. A foreseeable implementation for making the chassis portable is to have a handle on the chassis.

In some embodiments, the spraying means for spraying the anti-bacterial photocatalytic coating liquid has more than one spray heads, in order to provider a wider width coverage of spraying with a single passing of the apparatus over a surface area.

In some embodiments, the means for shining UV light onto the surface sprayed with the anti-bacterial photocatalytic coating liquid uses an elongated UV light. In some other embodiments, the baking means chassis for baking the surface sprayed with the anti-bacterial photocatalytic coating liquid uses an elongated IR (infra-red) light.

In another aspect, anti-bacterial photocatalytic coating process comprises four steps. Step 1 is the applying of plasma surface activation onto a stationary surface. Step 2 is the spraying of an anti-bacterial photocatalytic coating liquid onto the same surface. Step 3 is the shining of UV light onto the surface sprayed with the anti-bacterial photocatalytic coating liquid. Step 4 is an optional step, baking the surface sprayed with the anti-bacterial photocatalytic coating liquid. Each of the step may be accomplished through different equipment. For example, when coating an anti-bacterial photocatalytic coating onto a stationary table in a fast-food restaurant, a hand-held plasma machine may be used on the tabletop for surface activation first during Step 1. On Step 2, a compressor-powered spraying machine may be used to spray an anti-bacterial photocatalytic coating liquid on the tabletop. On Step 3, a hand-held UV light equipment is used to shine on the tabletop. Finally and optionally on Step 4, a portable baking machine may be laying over the tabletop to baking it.

In another aspect, anti-bacterial photocatalytic coating process comprises four steps. Step 1 is the spraying a non-photocatalytic prime coating liquid onto a stationary surface. Step 2 is the spraying of an anti-bacterial photocatalytic coating liquid onto the same surface. Step 3 is the shining of UV light onto the surface sprayed with the anti-bacterial photocatalytic coating liquid. Step 4 is an optional step, baking the surface sprayed with the anti-bacterial photocatalytic coating liquid. Each of the step may be accomplished through different equipment. For example, when coating an anti-bacterial photocatalytic coating onto a stationary table in a fast-food restaurant, a hand-held plasma machine may be used on the tabletop for surface activation first during Step 1. On Step 2, a compressor-powered spraying machine may be used to spray an anti-bacterial photocatalytic coating liquid on the tabletop. On Step 3, a hand-held UV light equipment is used to shine on the tabletop. Finally and optionally on Step 4, a portable baking machine may be laying over the tabletop to baking it.

In some embodiments, the photocatalytic particles of the anti-bacterial photocatalytic coating liquid are photocatalytic activated by ambient light with at least 95% of a spectral power distribution (SPD) in a visible light wavelength range greater than 400 nm. In other words, once the stationary surface is coated with the anti-bacterial photocatalytic coating, the anti-bacterial protection may be activated by visible light in the environment such as sunlight or regular light bulb or lighting fixtures, without the need of using dedicated UV light source.

In some embodiments, the anti-bacterial photocatalytic coating liquid has at least 90% light transparency. This is to ensure the anti-bacterial photocatalytic coating doesn't alter the color and the texture of the underlying stationary surface.

In some embodiments, the anti-bacterial photocatalytic coating liquid is a water-based liquid, and more precisely, it comprises at least 95% net weight in water and less than 5% of net weight in photocatalytic particles. d In some embodiments, a main active ingredient of the anti-bacterial photocatalytic film is titanium dioxide ($TiO_2$). In some other embodiments the main active ingredient is rhombus-shape anatase-type titanium dioxide ($TiO_2$). As shown in U.S. Pat. No. 9,522,384 by Lu L. et al, the rhombus-shape anatase-type titanium dioxide has a much higher volume density than the sphere-shape anatase-type titanium dioxide, thus it is more effective in the photocatalytic killing of bacteria and viruses.

In some embodiments, the anti-bacterial photocatalytic film may contain at least one other active metal ingredient such as but not limited to, silver, gold, copper, zinc, or nickel. These metals when embedded in the photocatalyst are known to enhance the photocatalytic activity with visible light. Some photocatalytic film may contain more than one type of metals for a better photocatalytic effectiveness.

The titanium dioxide is classified as a semiconducting photocatalyst. Recently technology breakthrough has demonstrated that noble metal nanoparticles such as gold (Au) and silver (Ag) can are a class of efficient photocatalysts working by mechanisms distinct from those of semiconducting photocatalysts (https://pubs.rsc.org/en/content/article-landing/2013/gc/c3gc40450a#!divAbstract). The present disclosure is not limited to the use of semiconducting photocatalysts. In some embodiments, the main active ingredient of the anti-bacterial photocatalytic film is a noble metal nanoparticle comprising gold (Au) or sliver (Ag).

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

Example Implementations

Figure 1:
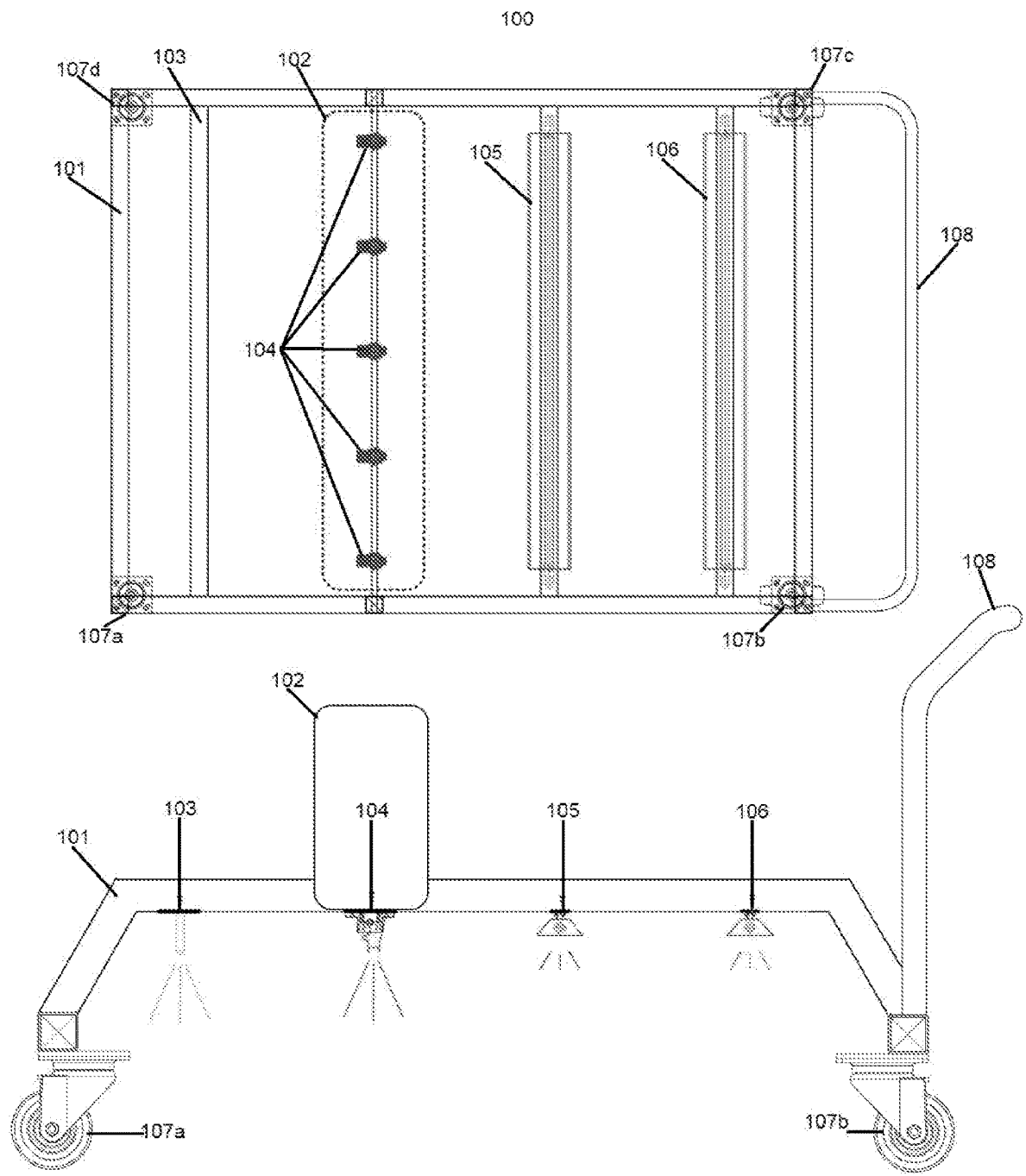
FIG. 1 schematically depicts a diagram of a moveable anti-bacterial photocatalytic coating apparatus.

The FIG. 1 is an embodiment of the anti-bacterial photocatalytic coating apparatus of the present disclosure 100, which includes a chassis 101 and a container 102 containing anti-bacterial photocatalytic coating liquid. A plasma injection head 103 is mounted on the chassis. Multiple stationary spray heads 104 are used for spraying the anti-bacterial photocatalytic liquid evenly onto the surface under the chassis with a single pass. Also mounted on the chassis are an elongated UV light 105 and an elongated IR light 106. The apparatus is on wheels 107a-107d and with a push-handle 108. During operation, the apparatus is pushed from right to left. So the plasma injection head 103 will hover over the untreated surface first. The plasma injection head 103 applies plasma to the plastic or rubber surface to activate the surface. Then the spray heads 104 spray the anti-bacterial photocatalytic liquid onto the surface activated by the plasma. The elongated UV light 105 then activates the photocatalytic particles on the surface and enhance the binding of the photocatalytic film onto the surface. Finally, the elongated IR light bakes and dries the anti-bacterial photocatalytic liquid. It is foreseeable to add a motor to the chassis so as to make it self-propelling. It is also foreseeable to add a control subsystem to control the self-propelling speed, the spray rate of the anti-bacterial photocatalytic liquid, the intensity of the UV light, and/or the temperature of the IR light.

Figure 2:
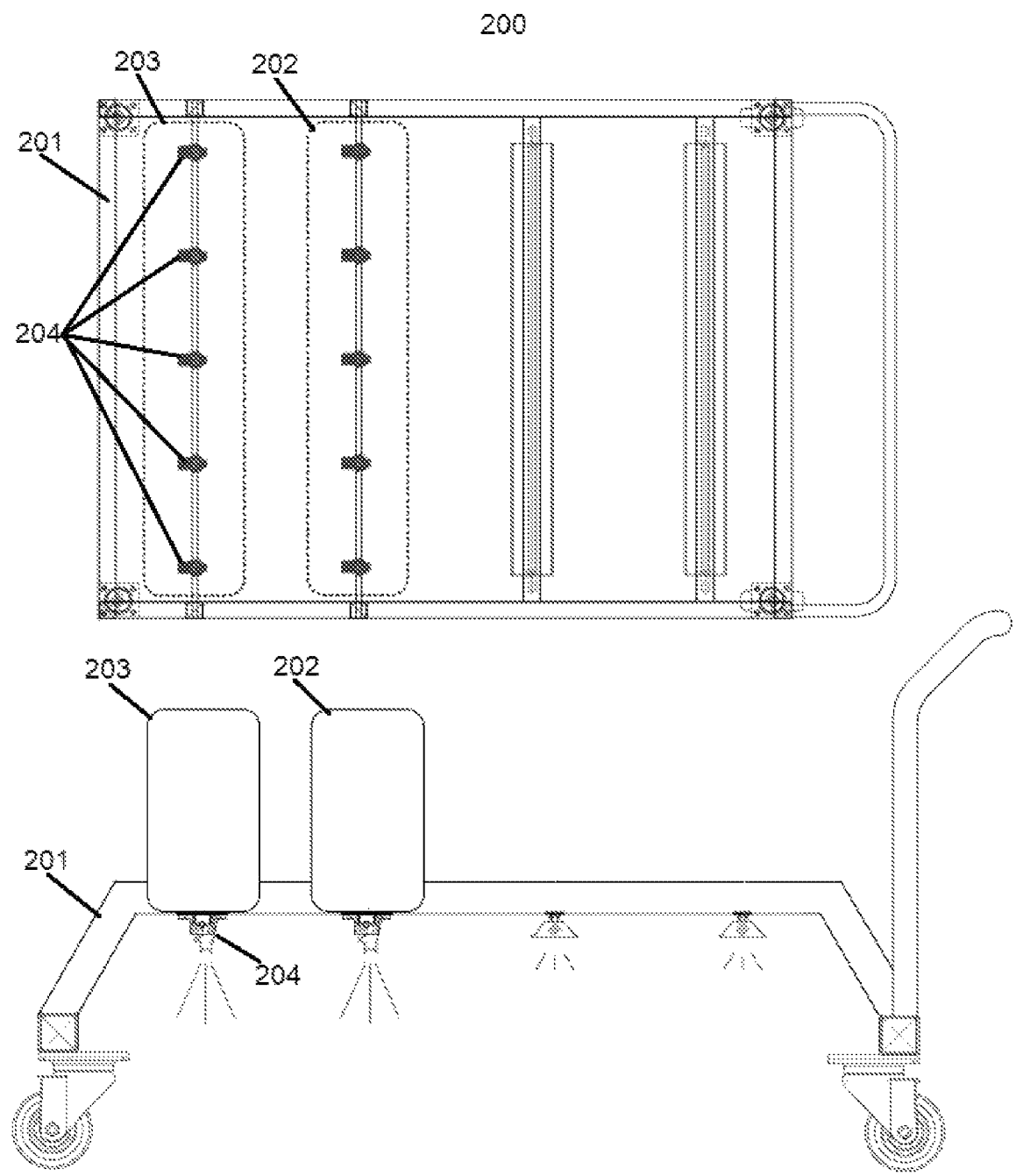
FIG. 2 schematically depicts a diagram of another anti-bacterial photocatalytic coating apparatus.

For ceramic, terra cotta, or concrete surface, plasma is not effectively in activating the surface for photocatalytic coating. A more suitable option for preparing the surface for photocatalytic coating is through the application of a prime coating. FIG. 2 is an embodiment of the anti-bacterial photocatalytic coating apparatus of the present disclosure 200, which includes a chassis 201 and a container 202 containing anti-bacterial photocatalytic coating liquid, and a container 203 containing the prime coating liquid. The plasma injection head 103 in FIG. 1 is now replaced with multiple spray heads 204 for spraying the prime coating. As the apparatus is moving from right to left in operation, the surface is underneath the chassis is first sprayed with the prime coating liquid, and followed by the spraying of the anti-bacterial photocatalytic coating liquid. It is foreseeable to add another baking/drying means between spraying of the prime coating liquid and the spraying of the anti-bacterial photocatalytic coating liquid so as to dry up the prime coating liquid appropriately before the spraying of the anti-bacterial photocatalytic coating liquid.

Figure 3:
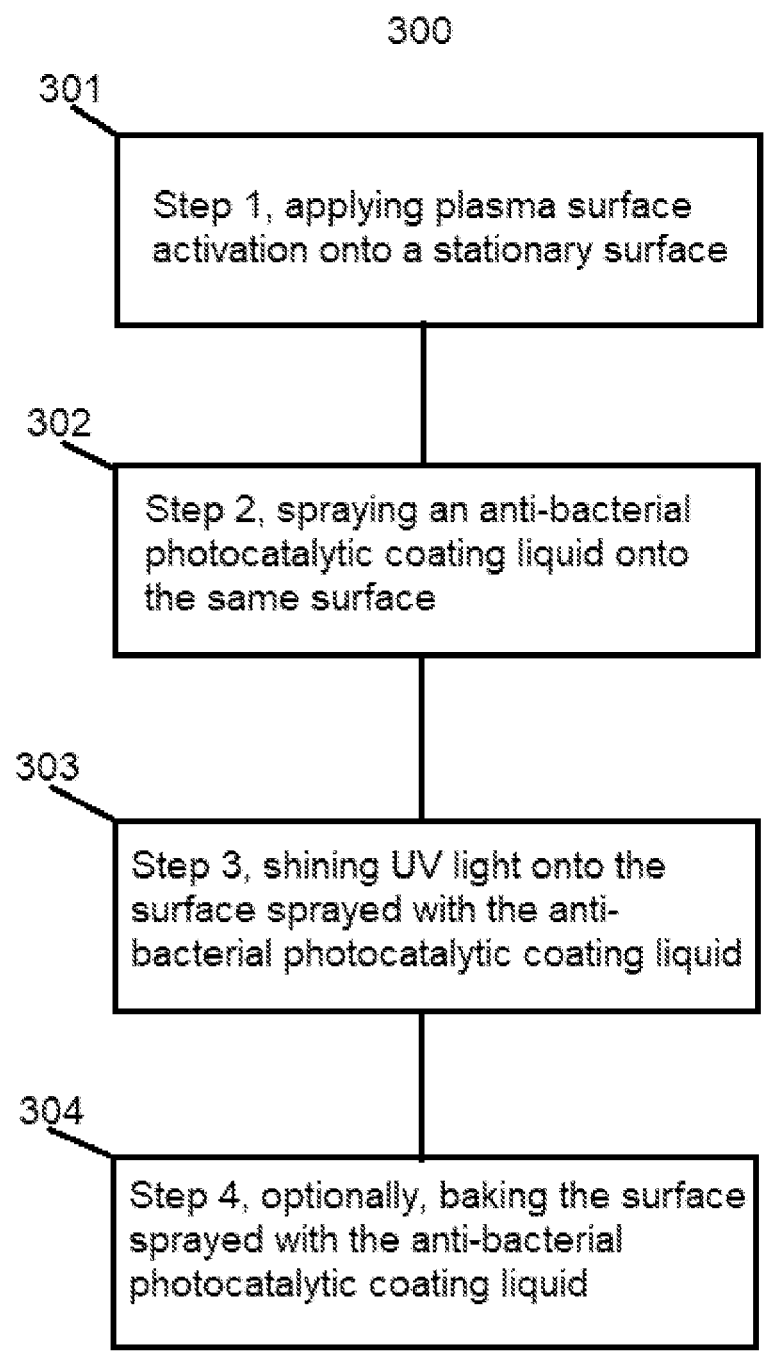
FIG. 3 schematically depicts a flowchart of an anti-bacterial photocatalytic coating process.

The FIG. 3 is a flowchart of the anti-bacterial photocatalytic coating process of the present disclosure 300 using plasma for surface activation. The process consists 4 steps. Step 1 301 is the applying plasma surface activation onto a stationary surface. Step 2 302 is the spraying a non-photocatalytic prime coating liquid onto a stationary surface. Step 3 303 is the shining UV light onto the surface sprayed with the anti-bacterial photocatalytic coating liquid. Then optionally, Step 4 304 is the baking the surface sprayed with the anti-bacterial photocatalytic coating liquid. The emphasis on the stationary surface is that this disclosure is meant for photocatalytic coating onto a pre-installed surface, as opposed to a photocatalytic coating process during manufacturing where the object to be coated is moving through the photocatalytic coating equipment. The Step 4 baking process is optional because natural curing (natural drying) of the anti-bacterial photocatalytic coating liquid is suitable for some surface material.

Figure 4:
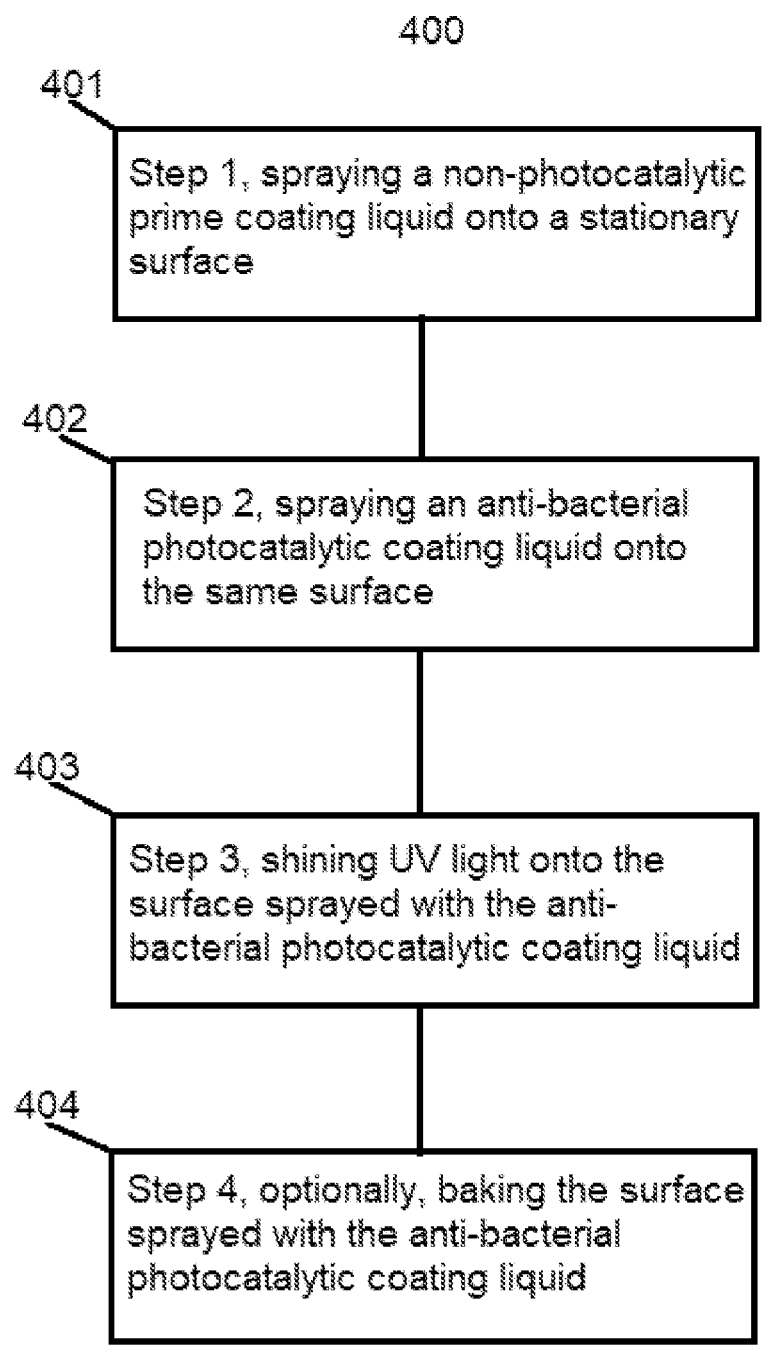
FIG. 4 schematically depicts a flowchart of an anti-bacterial photocatalytic coating process.

The FIG. 4 is a flowchart of the anti-bacterial photocatalytic coating process of the present disclosure 400 using a prime coating for surface preparation. The process consists 4 steps. Step 1 401 is the spraying a non-photocatalytic prime coating liquid onto a stationary surface. Step 2 402 is the spraying an anti-bacterial photocatalytic coating liquid onto a stationary surface. Step 3 403 is the shining UV light onto the surface sprayed with the anti-bacterial photocatalytic coating liquid. Then optionally, Step 4 404 is the baking the surface sprayed with the anti-bacterial photocatalytic coating liquid. It is foreseeable to add another baking/drying step between Step 1 and Step 2 so as to dry up the prime coating liquid appropriately before the spraying of the anti-bacterial photocatalytic coating liquid.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. An anti-bacterial photocatalytic coating apparatus, comprising:
   a chassis;
   a container containing an anti-bacterial photocatalytic coating liquid;
   means mounted on the chassis and capable of applying plasma-based surface activation onto a stationary underneath the chassis;
   means mounted on the chassis and capable of spraying the anti-bacterial photocatalytic coating liquid onto the plasma-activated surface underneath the chassis;
   means mounted on the chassis and capable of shining an ultraviolet (UV) light onto a surface sprayed with the anti-bacterial photocatalytic coating liquid; and
   optionally, means mounted on the chassis and capable of baking the surface sprayed with the anti-bacterial photocatalytic coating liquid,
   wherein the chassis is movable.

2. An anti-bacterial photocatalytic coating apparatus, comprising:
   a chassis;
   a container containing an anti-bacterial photocatalytic coating liquid; and
   a container containing a non-photocatalytic prime coating liquid;
   means mounted on the chassis and capable of spraying the non-photocatalytic prime coating liquid onto a stationary surface underneath the chassis;
   means mounted on the chassis and capable of spraying the anti-bacterial photocatalytic coating liquid onto the surface sprayed with the non-photocatalytic prime coating liquid;
   means mounted on the chassis and capable of shining an ultraviolet (UV) light onto the surface sprayed with the anti-bacterial photocatalytic coating liquid; and
   optionally, means mounted on the chassis and capable of baking the surface sprayed with the anti-bacterial photocatalytic coating liquid,
   wherein the chassis is movable.

3. The anti-bacterial photocatalytic coating apparatus of claim 1 or 2, further comprising means mounted to the chassis and capable of moving the chassis over the stationary surface.

4. The anti-bacterial photocatalytic coating apparatus of claim 1 or 2, wherein the chassis is portable by hand.

5. The anti-bacterial photocatalytic coating apparatus of claim 1, wherein the means mounted on the chassis and capable of spraying the anti-bacterial photocatalytic coating liquid comprises more than one spray heads.

6. The anti-bacterial photocatalytic coating apparatus of claim 1 or 2, wherein the means capable of shining the UV light onto the surface sprayed with the anti-bacterial photocatalytic coating liquid comprises an elongated UV light.

7. The anti-bacterial photocatalytic coating apparatus of claim 1 or 2, wherein the baking means comprises an elongated infrared (IR) light.

8. The anti-bacterial photocatalytic coating apparatus of claim 1 or 2, wherein photocatalytic particles of the anti-bacterial photocatalytic coating liquid are photocatalytic activated by ambient light with at least 95% of a spectral power distribution (SPD) in a visible light wavelength range greater than 400 nm.

9. The anti-bacterial photocatalytic coating apparatus of claim 1 or 2, wherein the anti-bacterial photocatalytic coating liquid has at least 90% light transparency.

10. The anti-bacterial photocatalytic coating apparatus of claim 1 or 2, wherein the anti-bacterial photocatalytic coating liquid comprises at least 95% net weight of water and less than 5% of net weight of photocatalytic particles.

11. The anti-bacterial photocatalytic coating apparatus of claim 1 or 2, wherein a main active ingredient of the anti-bacterial photocatalytic coating liquid comprises titanium dioxide ($TiO_2$).

12. The anti-bacterial photocatalytic coating apparatus of claim 11, wherein the main active ingredient of the anti-bacterial photocatalytic coating liquid comprises rhombus-shaped anatase-type titanium dioxide ($TiO_2$).

13. The anti-bacterial photocatalytic coating apparatus of claim 12, wherein the anti-bacterial photocatalytic coating liquid contains at least one other active metal ingredient comprising silver, gold, copper, zinc, nickel, or a combination thereof.

14. The anti-bacterial photocatalytic coating apparatus of claim 1 or 2, wherein a main active ingredient of the anti-bacterial photocatalytic coating liquid comprises a noble metal nanoparticle comprising gold (Au) or sliver (Ag).

\* \* \* \* \*